(12) United States Patent
Tenne et al.

(10) Patent No.: US 9,877,806 B2
(45) Date of Patent: Jan. 30, 2018

(54) LOW FRICTION COATINGS FOR USE IN DENTAL AND MEDICAL DEVICES

(75) Inventors: Reshef Tenne, Rehovot (IL); Alon Katz, Jerusalem (IL); Meir Redlich, Tel Aviv (IL); Lev Rapoport, Lod (IL)

(73) Assignees: YEDA RESEARCH AND DEVELOPMENT CO. LTD., Rehovot (IL); HADASIT MEDICAL RESEARCH SERVICE AND DEVELOPMENT LTD., Jerusalem (IL); HOLON ACADEMIC INSTITUTE OF TECHNOLOGY, Holon (IL)

( * ) Notice: Subject to any disclaimer, the term of this patent is extended or adjusted under 35 U.S.C. 154(b) by 1763 days.

(21) Appl. No.: 11/920,356

(22) PCT Filed: May 17, 2006

(86) PCT No.: PCT/IL2006/000578
§ 371 (c)(1),
(2), (4) Date: Jul. 31, 2008

(87) PCT Pub. No.: WO2006/123336
PCT Pub. Date: Nov. 23, 2006

(65) Prior Publication Data
US 2009/0032499 A1 Feb. 5, 2009

Related U.S. Application Data

(60) Provisional application No. 60/681,443, filed on May 17, 2005.

(51) Int. Cl.
*F16C 31/00* (2006.01)
*C10M 125/22* (2006.01)
(Continued)

(52) U.S. Cl.
CPC .......... *A61C 7/20* (2013.01); *A61C 7/14* (2013.01); *A61C 8/0013* (2013.01);
(Continued)

(58) Field of Classification Search
CPC .......... C22C 32/0089; B22F 3/114; Y10T 428/12028
(Continued)

(56) References Cited

U.S. PATENT DOCUMENTS 3,936,577 A * 2/1976 Christini et al. .............. 428/614
5,035,618 A   7/1991 Katz et al.
(Continued)

FOREIGN PATENT DOCUMENTS

CN   101227871 A   7/2008
EP   0 580 019 A1   1/1994
(Continued)

OTHER PUBLICATIONS

Chen et al. (2002). Advanced Engineering Materials, 4(9):686-690. *Wear and Friction of Ni-P Electroless Composite Coating Including Inorganic Fullerene-$WS_2$ Nanoparticles.*
(Continued)

*Primary Examiner* — Ellen S Wood
(74) *Attorney, Agent, or Firm* — Mark Cohen; Pearl Cohen; Zedek Latzer Baratz LLP

(57) ABSTRACT

The present invention provides an article, at least part of it being coated by inorganic fullerene-like (IF) nanoparticles or composite containing such nanoparticles. Preferably, the invention provides an article made of metal, for use in dentistry or medicine e.g. archwire, needle or catheter, having a friction-reducing film, and methods for coating such articles with a friction-reducing film.

28 Claims, 8 Drawing Sheets

(51) Int. Cl.
| | |
|---|---|
| A61C 7/20 | (2006.01) |
| A61C 7/14 | (2006.01) |
| A61C 8/00 | (2006.01) |
| A61L 27/30 | (2006.01) |
| A61L 29/10 | (2006.01) |
| A61L 31/08 | (2006.01) |
| C23C 18/32 | (2006.01) |
| C25D 3/56 | (2006.01) |
| C25D 5/34 | (2006.01) |
| C25D 15/02 | (2006.01) |
| C23C 18/16 | (2006.01) |

(52) U.S. Cl.
CPC ............ *A61L 27/303* (2013.01); *A61L 29/103* (2013.01); *A61L 31/084* (2013.01); *C23C 18/1662* (2013.01); *C23C 18/32* (2013.01); *C25D 3/562* (2013.01); *C25D 5/34* (2013.01); *C25D 15/02* (2013.01); *C23C 18/165* (2013.01); *Y10T 428/13* (2015.01); *Y10T 428/264* (2015.01); *Y10T 428/31511* (2015.04); *Y10T 428/31609* (2015.04); *Y10T 428/31678* (2015.04); *Y10T 428/31855* (2015.04)

(58) Field of Classification Search
USPC ........ 428/403, 614, 34.1; 508/103, 107, 108
See application file for complete search history.

(56) References Cited

U.S. PATENT DOCUMENTS

| | | | |
|---|---|---|---|
| 5,215,461 A | 6/1993 | Riazi | |
| 5,232,361 A | 8/1993 | Sachdeva et al. | |
| 5,288,230 A | 2/1994 | Nikutowski et al. | |
| 5,344,457 A * | 9/1994 | Pilliar et al. | 606/60 |
| 5,454,716 A | 10/1995 | Banerjee et al. | |
| 5,868,570 A | 2/1999 | Hickok et al. | |
| 5,877,243 A | 3/1999 | Sarangapani | |
| 5,958,358 A | 9/1999 | Tenne et al. | |
| 6,164,831 A | 12/2000 | Matsui et al. | |
| 6,299,438 B1 * | 10/2001 | Sahagian et al. | 433/6 |
| 6,409,506 B1 | 6/2002 | Graybill | |
| 6,575,747 B1 | 6/2003 | Riitano et al. | |
| 6,710,020 B2 * | 3/2004 | Tenne et al. | 508/103 |
| 6,910,889 B1 | 6/2005 | Hickok | |
| 2001/0034005 A1 | 10/2001 | Matsutani et al. | |
| 2003/0144155 A1 | 7/2003 | Tenne et al. | |
| 2004/0109823 A1 | 6/2004 | Kaplan | |
| 2004/0173378 A1 | 9/2004 | Zhou et al. | |
| 2007/0015107 A1 | 1/2007 | Mannschedel et al. | |
| 2007/0284255 A1 | 12/2007 | Gorokhovsky et al. | |
| 2008/0195196 A1 | 8/2008 | Asgari | |
| 2009/0032499 A1 | 2/2009 | Tenne et al. | |
| 2010/0105004 A1 | 4/2010 | Levy et al. | |
| 2013/0040261 A1 | 2/2013 | Kwon et al. | |

FOREIGN PATENT DOCUMENTS

| | | |
|---|---|---|
| GB | 2 360 790 A | 10/2001 |
| JP | 64-83252 A | 3/1989 |
| JP | 1-176097 A | 7/1989 |
| JP | 6-292690 A | 10/1994 |
| JP | 7-69782 A | 3/1995 |
| JP | 11-501543 A | 2/1999 |
| JP | 11-244307 A | 9/1999 |
| JP | 11-287250 A | 10/1999 |
| JP | 3116072 B2 | 10/2000 |
| JP | 2003-526001 A | 9/2003 |
| JP | 2004-526109 A | 8/2004 |
| WO | 96/27334 A1 | 9/1996 |
| WO | 97/44278 | 11/1997 |
| WO | WO 97/44278 | 11/1997 |
| WO | 01/66676 A2 | 9/2001 |
| WO | 02/079686 A2 | 10/2002 |
| WO | WO 2006/123336 | 11/2006 |
| WO | WO 2007/008243 | 1/2007 |

OTHER PUBLICATIONS

Rapoport et al. (2003). Wear, 255:785-793. *Tribological properties of $WS_2$ nanoparticles under mixed lubrication.*

Redlich et al. (2003). American Journal of Orthodontics and Dentofacial Orthopedics, 124: 69-73. *In vitro study of frictional forces during sliding mechanics of "reduced-friction" brackets.*

Tenne et al. (1992). Letters to Nature, 360: 444-445. *Polyhedral and cylindrical structures of tungsten disulphide.*

Katz et al. (2006). Tribology Letters, vol. 21, No. 2. *Self-lubricating coatings containing fullerene-like $WS_2$ nanoparticles for orthodontic wires and other possible medical applications.*

Chen, et al., "Wear and Friction of Ni-P Electroless Composite Coating Including Inorganic Fullerene-WS2 Nanoparticles", Advanced Engineering Materials, vol. 4, No. 9, pp. 686-690, (2002).

The Supplementary European Search Report for corresponding EP Application No. 06 74 5103; three pages; search completed Nov. 16, 2012.

Alapati et al. "SEM observations of nickel-titanium rotary endodontic instruments that fractured during clinical use" Journal of Endodontics. Jan. 31, 2005;31(1):40-3.

Anderson et al. "Fracture resistance of electropolished rotary nickel-titanium endodontic instruments" Journal of Endodontics. Oct. 31, 2007;33(10):1212-6.

Bojda et al. "Precipitation of Ni 4 Ti 3-variants in a polycrystalline Ni-rich NiTi shape memory alloy" Scripta materialia. Jul. 31, 2005;53(1):99-104.

Brinson et al. "Stress-induced transformation behavior of a polycrystalline NiTi shape memory alloy: micro and macromechanical investigations via in situ optical microscopy" Journal of the Mechanics and Physics of Solids. Jul. 31, 2004;52(7):1549-71.

Cheung et al. "Defects in ProTaper S1 instruments after clinical use: fractographic examination" International Endodontic Journal. Nov. 1, 2005;38(11):802-9.

Eggeler et al. "Wagner M. Structural and functional fatigue of NiTi shape memory alloys" Materials Science and Engineering: A. Jul. 25, 2004;378(1):24-33.

Friedman et al. "Fabrication of self-lubricating cobalt coatings on metal surfaces" Nanotechnology. Feb. 7, 2007;18(11):115703.

Kuhn et al. "Influence of structure on nickel-titanium endodontic instruments failure" Journal of Endodontics. Aug. 31, 2001;27(8):516-20.

Liu et al. "Effect of deformation by stress-induced martensitic transformation on the transformation behaviour of NiTi" Intermetallics. Jan. 31, 2000;8(1):67-75.

Morgan "Medical shape memory alloy applications—the market and its products" Materials Science and Engineering: A. Jul. 25, 2004;378(1):16-23.

Nayan et al. "Effect of mechanical cycling on the stress-strain response of a martensitic Nitinol shape memory alloy" Materials Science and Engineering: A. Nov. 15, 2009;525(1):60-7.

Otsuka et al. "Physical metallurgy of Ti—Ni-based shape memory alloys" Progress in materials science. Jul. 31, 2005;50(5):511-678.

Parashos et al. "Rotary NiTi instrument fracture and its consequences" Journal of Endodontics. Nov. 30, 2006;32(11):1031-43.

Pelletier et al. "Structural and mechanical characterisation of boron and nitrogen implanted NiTi shape memory alloy" Surface and Coatings Technology. Sep. 30, 2002;158:309-17.

Pelton et al. "Nitinol Medical Devices" Advanced Materials & Processes. 2005, 163(10): 36-65.

Peters OA, "Current challenges and concepts in the preparation of root canal systems: a review" Journal of endodontics, Aug. 31, 2004;30(8):559-67.

Peters et al. "Effect of liquid and paste-type lubricants on torque values during simulated rotary root canal instrumentation" International endodontic journal. Apr. 1, 2005;38(4):223-9.

(56) References Cited

OTHER PUBLICATIONS

Rapoport et al. "Hollow nanoparticies of WS 2 as potential solid-state lubricants" Nature. Jun. 19, 1997;387(6635):791-3.
Rapoport et al. "Applications of WS 2 (MoS 2) inorganic nanotubes and fullerene-like nanoparticles for solid lubrication and for structural nanocomposites" *Journal of Materials Chemistry*, 2005, 15(18), pp. 1782-1788.
Sattapan et al. "Defects in rotary nickel-titanium files after clinical use" Journal of Endodontics. Mar. 31, 2000;26(3):161-5.
Spanaki-Voreadi et al. "Failure mechanism of ProTaper Ni—Ti rotary instruments during clinical use: fractographic analysis" International Endodontic Journal, Mar. 1, 2006;39(3):171-8.
Tenne et al. "inorganic nanotubes and fullerenc like nanoparticles" Nat Nanotechnol. Nov. 2006;1(2):103-11.
Thompson SA. "An overview of nickel-titanium alloys used in dentistry" International endodontic journal. Jul. 1, 2000;33(4):297-310.
Yared et al. "Influence of rotational speed, torque and operator's proficiency on ProFile failures" International Endodontic Journal. Jan. 1, 2001;34(1):47-53.

\* cited by examiner

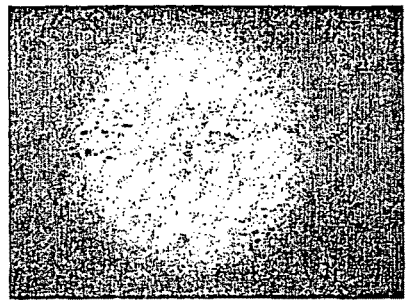
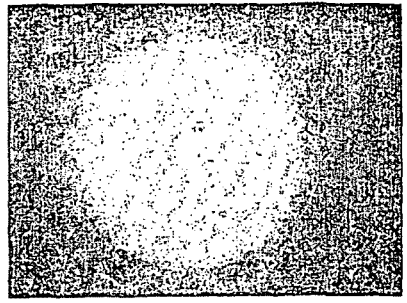
FIG. 5A                FIG. 5B
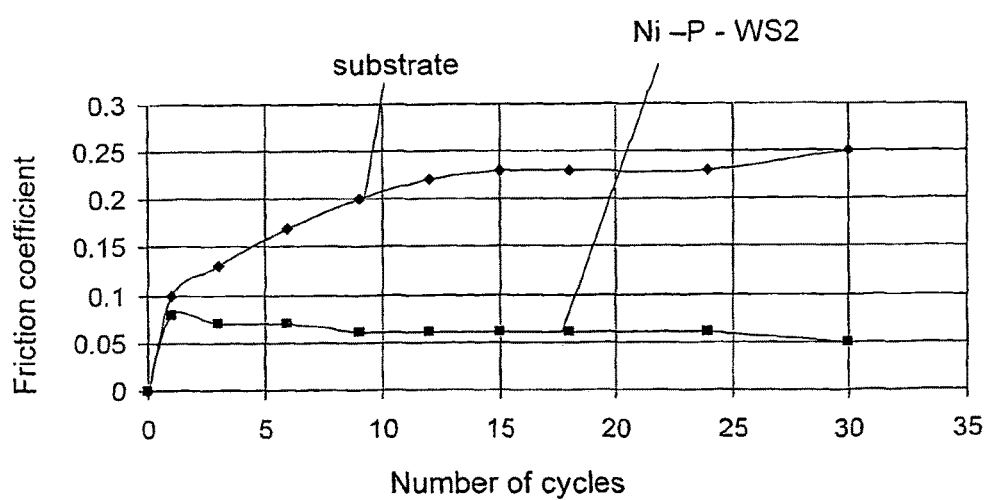
FIG. 6 bracket

LOW FRICTION COATINGS FOR USE IN DENTAL AND MEDICAL DEVICES

CROSS-REFERENCE

This is a National Phase Application filed under 35 U.S.C. 371 of International Application No. PCT/IL2006/000578, filed May 17, 2006, claiming the benefit under 35 USC 119(e) of U.S. Provisional Application No. 60/681,443, filed May 17, 2005, the entire contents of each of which is hereby incorporated herein by reference in its entirety.

FIELD OF THE INVENTION

This invention relates to the field of dental and medical articles, such as orthodontic archwires, brackets, catheters, implants and needles. More specifically, the invention relates to dental articles and articles for use in medicine in general, having a friction-reducing coating.

LIST OF REFERENCES

The following references are considered to be pertinent for the purpose of understanding the background of the present invention:
Chen et al, Adv. Eng. Mat. 4(9):686-690 (2002);
L. Rapoport et al, Wear 255:785-793 (2003);
Redlich et al., Am. J. Orthod. Dentofacial Orthop. 124, 69-73 (2003);
Tenne R. et al, Nature 360: 444-445 (1992);
U.S. Pat. No. 5,288,230;
U.S. Pat. No. 5,454,716;
U.S. Pat. No. 5,958,358; and
U.S. Pat. No. 6,299,438.

BACKGROUND OF THE INVENTION

Many articles: are currently produced bearing a low-friction coating, among them articles used in medicine and dentistry e.g. in orthodontics. Orthodontics is a dental specialty, which aims to bring about changes in the location of abnormally positioned teeth. This is achieved by application of continuous mechanical load (orthodontic force) on the tooth, which affects the periodontal ligament (PDL) and the alveolar bone surrounding the tooth. The applied force brings about remodeling of the PDL and the bone, which enables the transposition of the tooth. The orthodontic treatment has become very common in recent decades and also adults have begun seeking this treatment for esthetic and functional reasons.

The most common orthodontic technique consists of a rigid wire (also termed "archwire"), which is inserted into slots incorporated within special attachments (orthodontic brackets) being bonded on the teeth, as illustrated in FIG. 1. The basic principle of orthodontic appliances in the archwire technique is to apply mechanical forces on teeth so that movement will occur in every desirable spatial direction. The forces are applied during the various stages of treatment by a variety of appliances, which include several kinds of archwire, ligatures, brackets and bands.

Friction among appliances used for orthodontic correction of teeth is recognized by clinicians as a hindrance to tooth movement. Friction reduces the effective force, which is applied to the tooth from the wire. In the case of sliding mechanics, excessive friction, brought about by the angle between the wire and the slot of the bracket, slows tooth movement down substantially or even halts it. A frictional type force that resists the movement of the tooth and accompanies the sliding of a tooth along an archwire is referred to as resistance to sliding (RS).

There are a number of factors that may influence the RS directly and indirectly:
1. The archwire: size, shape, material and surface.
2. The bracket: material, size and shape of the slot and its edges, surface of slot and the angle formed between the wire and the slot.
3. Ligation of the wire in the slot: elastic module, metal wire ligature and self-ligating brackets.
4. Intraoral factors: saliva, plaque and corrosion.
5. Other factors: distance between teeth and direction of the applied force.

Over the years attempts have been made by researchers and manufacturers to reduce the friction. The problem was approached from different aspects:
1. Reduction of the size of the wire compared to the slot or the use of round wires, reduced friction to some extent but resulted in wire distortion that impaired the control of the direction of tooth movement.
2. Use of different metals (archwire or bracket) trying to reduce the coefficient of friction. The use of nickel-titanium wire has a major advantage in arch alignment due to its shape memory quality but the friction on these wires is higher compared to stainless steel (SS) wires.
3. The method of ligating the wire to the slot can reduce function. This was shown to be true with the self-ligating brackets at a 0° angle, but higher friction was recorded once the wire contacted the slot walls.

Coating thin films of various materials onto archwires has been previously suggested as another way to reduce friction and to improve their aesthetic appearance. U.S. Pat. No. 5,288,230 describes applying a coating of diamond-like carbon (DLC) onto archwires to serve as a barrier to diffusion of nickel and chromium from the wire and also provide a hard, friction-reducing surface. U.S. Pat. No. 5,454,716 describes a coating of a plastic-ceramic composite, which is aesthetically pleasing, but is susceptible to localized abrasion over time. Another method is described in U.S. Pat. No. 6,299,438 and comprises applying a function-reducing coating containing iridium or platinum to a metal and/or ceramic dental article which is first coated with an adhesion metal layer.

Another function problem commonly encountered in dentistry is related to screw-type dental implants, between the implant and the bone walls into which the implant is inserted. Screw-type dental implants are made in two general types. The first type is a self-tapping implant that can be threaded into a pre-drilled bore in a jawbone without pre-tapping the bore. The second type is a non-self-tapping implant that requires pre-tapping of the bore. In either type, the implant has a generally cylindrical main body which bears one or more external screw threads on its outer surface. These external thread(s) engage corresponding internal thread(s) cut into the wall of the bore to provide initial stabilization of the implant in the bore.

The friction encountered by dental implants is proportional to the penetration depth of the implant into the bone, the diameter of the bore, and the hardness of the bone at the site of the bore. The torque that must be applied to insert the implant into the bore is proportional to the friction. High torque puts strains on the implant, on the tools used to place the implant in the bore, and on the bone. Furthermore, in cases where high torque is required to insert the implant, there is a greater risk of damage to the implant, the tools, and the bone. Consequently, there is a continuing need to design a screw-type dental implant which minimizes the torque needed to install it into living jawbone.

SUMMARY OF THE INVENTION

It would be clinically advantageous to reduce friction forces during orthodontic or other medical treatment. In orthodontics, unimpeded tooth movement may reduce the time needed for treatment, thereby reducing the risks of adverse effects of wearing orthodontic article on the teeth and surrounding tissues. Also in medicine, coating tissue penetrating devices with low function coating may reduce tissue damage adjacent to these medical devices during the insertion procedure into tissues.

The present invention provides an article for use in medicine or dentistry, being coated at least partially by inorganic fullerene-like (IF) nanoparticles or a composite containing such nanoparticles. The coating, which may include inorganic fullerene-like (IF) nanoparticles or a composite containing inorganic fullerene-like (IF) nanoparticles, may have a thickness of between 0.3 micron and 50 microns. The coating may also have a thickness of between 1 micron and 10 microns.

The present invention provides an article for use in medicine or dentistry, being coated at least partially by inorganic fullerene-like (IF) nanoparticles or a composite containing such nanoparticles.

The present invention further provides methods for coating articles for use in medicine or dentistry with inorganic fullerene-like (IF) nanoparticles or a composite containing such nanoparticles.

In a first of its aspects, the present invention thus provides an article, preferably elongated, at least part of it being coated by inorganic fullerene-like (IF) nanoparticles or composite containing IF nanoparticles. The inorganic fullerene-like (IF) particles are self-lubricating and thus reduce function between the article and adjacent object, surface or tissue, as compared to uncoated article.

The article of the present invention is preferably made of metal, plastic, rubber or glass. More preferably, the article is made of metal.

An "elongated article" within the context of the present invention is an article extending preliminarily along one axis (i.e. length) while having smaller dimensions along the other perpendicular two axes (i.e. thickness and cross-section). In a preferred embodiment of the invention the elongated article has a cross-section in the range of about a centimeter or less, preferably of about several millimeters or less. Nevertheless, elongated articles with cross-sections larger than about a centimeter are also within the scope of the invention, as long as they are used in medicine or dentistry. Non limiting examples of elongated articles are needles, catheters and archwires.

In a preferred embodiment of the invention, the coated article is used in dentistry e.g. in orthodontic appliances or dental implants. For orthodontic uses the article is either circular or rectangular in cross-section and has the form of a wire or elongated hollow tube. In these uses at least part of the article of the invention is coated by friction reducing film comprising inorganic fullerene-like (LF) nanoparticles or composite containing IF nanoparticles.

The term "wire" as used herein includes, for example, an archwire used in orthodontics.

The term "inorganic fullerene-like (IF) particles" or "inorganic fullerene-like (IF) nanoparticles" within the context of the present invention covers hollow and non-hollow nanoparticles of transition metal chalcogenides and dichalcogenides, made up of single or multi-layers and having structures such as spheres, tubes, nested polyhedra, onion-like and the like.

A "transition metal" includes all the metals in the periodic table from titanium to copper, from zirconium to silver and from hafnium to gold. Preferably, the transition metals are selected from Mo, W, V, Zr, Hf, Pt, Pd, Re, Nb, Ta, Ti, Cr and Ru.

A "chalcogen" as used herein refers to S, Se or Te.

The metal chalcogenides and dichalcogenides are preferably selected from $TiS_2$, $TiSe_2$, $TiTe_2$, $WS_2$, $WSe_2$, $WTe_2$, $MoS_2$, $MoSe_2$, $MoTe_2$, $SnS_2$, $SnSe_2$, $SnTe_2$, $RuS_2$, $RuSe_2$, $RuTe_2$, GaS, GaSe, GaTe, InS, InSe, $HfS_2$, $ZrS_2$, $VS_2$, $ReS_2$ and $NbS_2$. More preferably, the metal chalcogenides and dichalcogenides are selected from $WS_2$ and $MoS_2$.

Inorganic fullerene-like $WS_2$ (IF-$WS_2$) was first reported by Tenne and co-workers in 1992 [Tenne R. et al, Nature 360: 444-445 (1992) and U.S. Pat. No. 5,958,358]. It was shown that under a certain reducing and sulfidizing atmosphere at elevated temperatures, tungsten oxide nanoparticles could fold and form nested $WS_2$ fullerene-like nanostructures with layers that resemble an onion. The size of these nanoparticles range from tens to several hundreds of nanometers, depending on the $WO_3$ precursor's size.

Surprisingly, the inventors have found that IF particles are biocompatible. Consequently, and in view of their superior tribological properties, as compared to same particles in platelet form [L. Rapoport et al, Wear 255:785-793 (2003)], these biocompatible IF particles may be used in biological systems in humans to alleviate friction problems. Consequently, the present invention provides in one of its aspects, biocompatible article, preferably made of metal, at least part of it being coated by friction reducing film comprising inorganic fullerene-like (IF) particles or composite containing IF particles.

"Biocompatible article" is defined for purposes of this description as article that can be used in animals, particularly humans without a significant adverse biological (e.g., toxic, inflammatory, carcinogenic, or immunogenic) host response (e.g., foreign body reaction, autoimmune disease, necrosis, apoptosis) whether delayed or immediate.

A preferred embodiment of the present invention also provides an improved screw-type dental implant that reduces the torque required to install the implant by reducing the friction between the implant and the sidewalls of the bore, at least a portion of the implant being coated by friction reducing film comprising inorganic fullerene-like (IF) particles or composite containing IF particles.

The term "composite" as used herein refers to solid material made from two or more components. One component is often fibers or particles, such as graphite fibers, BN-whiskers and IF-nanoparticles, that give the material its tensile strength, while another component (called a matrix), such as Ni—P, polyurethane and epoxy, binds the fibers or particles together. Non-limiting examples of composite according to the present invention are Ni—P-IF-nanoparticles, any metal film, like Pt containing IF-nanoparticles, polymer (e.g. polyurethane or polypropylene) or epoxy containing IF-nanoparticles or a sol-gel glass containing IF-nanoparticles.

The term "friction-reducing film" refers to a film or layer of an article capable to reduce the surface friction coefficient of that article, as measured with a ball-on-flat device by at least 20% when compared to the friction coefficient of the uncoated article.

The article of the invention being coated at least partially with a friction reducing film is used in dentistry and medicine and is selected from all types and sizes of orthodontic archwires, all types of orthodontic brackets, dental implants, bands, all types of bonded or banded orthodontic attachments and, palatal expanders used to orthodontically expand lower and upper dental dentitions. The friction reducing film can be also used to reduce friction in mobile functioning native or artificial human joints including temporo-mandibular joint, knee, ankle, elbow etc and also in hip replacement. Coating needles or catheters, which penetrate human tissues, with the friction reducing film of the invention will significantly reduce tissue damage adjacent to these medical devices during the insertion procedure. Further uses of low friction medical instruments are feeding oral and nasal tubes as well as the various tubes used for laparoscopic surgeries. The articles may be made of any metals suitable for use in dental and medical devices, for example stainless steel, iridium, platinum, palladium, rhodium, rhenium, alumina, zirconia, nickel-titanium, gold, silver, titanium, titanium-molybdenum alloy (TMA), beta-titanium and blends or alloys of these.

The function reducing film comprises biocompatible LP nanoparticles or composite containing such nanoparticles, capable of reducing the surface friction of the coated article (compared to the uncoated article) so that metal pieces e.g. pieces of the dental article which are connected together and cooperate with each other, e.g., archwires and brackets, can slide past each other more easily, thereby allowing for easier and more precise adjustment by the orthodontist or dentist. The coating preferably also has the properties of being resistant to mechanical wear and sufficiently inert to resist degradation in the environment of the mouth.

In order to utilize the properties of the IF-nanoparticles to reduce the friction in biological systems, the inventors developed a method for reducing friction between an article used in medicine or dentistry and adjacent surface, tissue or object, by coating at least part of the article's surface by inorganic fullerene-like (IF) nanoparticles or composite containing such nanoparticles.

According to a further aspect thereof, the present invention provides a method for reducing friction between a dental article and other articles or the tooth, said article being selected from dental implant, orthodontic wire, orthodontic bracket, band, bonded or banded orthodontic attachment, palatal expanders, the method comprising coating at least part of the article's surface with a friction-reducing film, said film comprising inorganic fullerene-like (IF) nanoparticles or composite containing such nanoparticles.

It should be noted that the method is preferably adapted for coating wires and similar tubular structures that are characterized by different morphologies in comparison to flat substrates.

According to another aspect thereof, the present invention provides a method for coating an article for use in medicine or dentistry with a friction reducing film, the method comprising:

(i) dispersing IF nanoparticles within a plating solution to obtain IF nanoparticles homogeneously dispersed in said plating solution;

(ii) contacting the article with said plating solution and depositing said nanoparticles on one or more surfaces of said article through electroless or electrochemical deposition, thereby obtaining an article coated on at least part of its surfaces with a friction reducing film comprising IF nanoparticles or composite containing such nanoparticles.

According to a preferred embodiment of the invention, the method comprises prior to contacting the article with the plating solution exposing the article to a surface pre-treatment procedure. Preferably, the pre-treatment procedure is carried out with an etching acidic solution, for example HF etching solution.

According to another preferred embodiment of the invention, the method comprises one or more additional deposition steps prior to said contacting to form intermediate layers between the article and the outer, friction reducing film.

According to a preferred embodiment of the invention, the method further comprises annealing the coated article at high temperature.

Preferably, the article is a metallic wire. More preferably, the wire is a wire used in orthodontic appliances and is usually made of stainless steel, iridium, platinum, palladium, rhodium, rhenium, gold, silver and blends or alloys of these.

In a preferred embodiment of the invention, the article is also exposed to e-beam deposition of Ni—Cr and/or Ni before the deposition of the friction reducing film.

The friction reducing film may be applied by any technique which is useful for depositing metallic coatings onto metallic substrates, for example, electroless deposition and electrodeposition, sputtering, chemical vapor deposition, ion beam enhanced deposition, plasma-assisted vapor deposition, cathodic arc deposition, ion implantation and evaporation, most preferably being electroless deposition and electrodeposition.

In a preferred embodiment where electroless deposition is applied, the plating solution comprises Ni or Co, phosphate or borate salt, reducing agent e.g. citrate, and surfactant and the article obtained by the method of the invention is coated with a friction-reducing film comprising composite of Ni—P, Co—P, Ni—B or Co—B and IF nanoparticles.

In another embodiment of the invention the article is coated with a polymer (e.g. polyurethane or polypropylene) or epoxy coating.

In a further embodiment of the invention, a sol-gel glass coating is applied on the article.

According to one embodiment of the invention, the article is coated with IF-nanoparticles. For implementing this embodiment, nanoparticles powder, such as IF-$WS_2$ powder, may be burnished with cloth for 15 minutes and then the article may be also burnished with the cloth until a thin coating of the IF-$WS_2$ is applied on the article, which serves as a self-lubricating coating.

BRIEF DESCRIPTION OF THE DRAWINGS

In order to understand the invention and to see how it may be carried out in practice, a preferred embodiment will now be described, by way of non-limiting examples only, with reference to the accompanying drawings, in which:

FIG. 5 shows optical micrographs of the surface of $Si_3N_4$ ball after the friction with Ni—P-IF coating using Mouth Kote fluid (A)—Before cleaning, (B)—After cleaning.

FIG. 6 is a graph showing the friction coefficient of the orthodontic wire vs. number of cycles, compared to a wire coated with Ni—P—$WS_2$ composite.

DETAILED DESCRIPTION OF EXEMPLARY EMBODIMENTS

Figure 1:
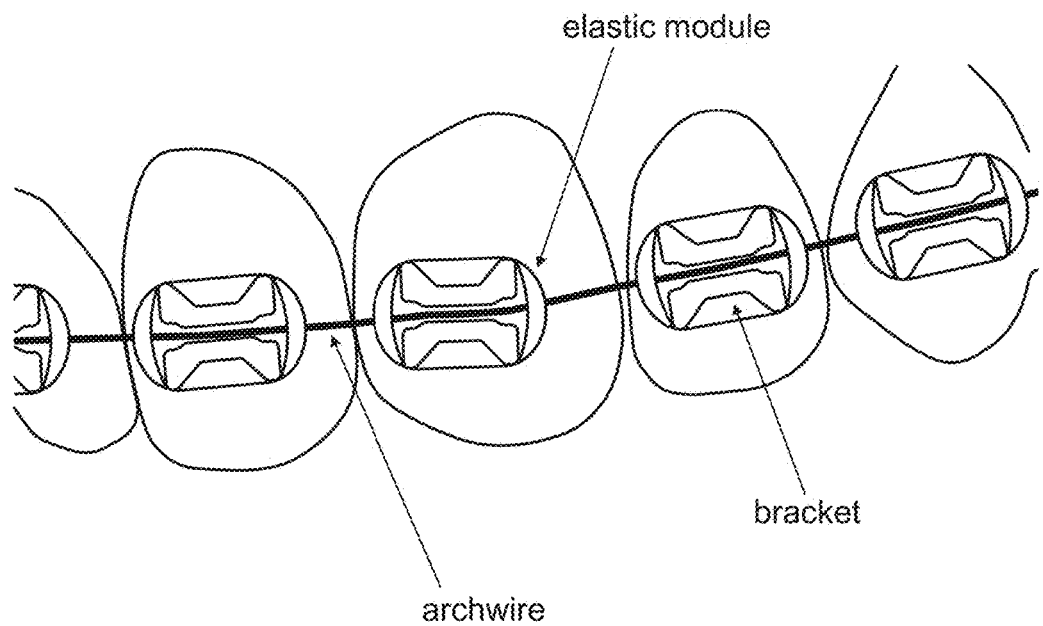
FIG. 1 is a photograph illustrating the orthodontic setup of a fixed orthodontic appliance.

The present invention provides an article for use in medicine or dentistry, preferably made of metal, at least part of its surface being coated by friction reducing film comprising inorganic fullerene-like (IF) nanoparticles or composite containing such IF nanoparticles.

The article may be, for example, an elongated article such as a metallic wire e.g. orthodontic archwire or elongated medical article e.g. needle, catheter, etc.

The present invention further provides methods for coating the articles with a friction-reducing film which comprises IF nanoparticles or composite containing such nanoparticles.

When the article is a dental article, it may comprise a metallic article which is placed temporarily or permanently in the mouth of an individual. Such articles include, for example, orthodontic appliances such as archwires or screw-type dental implants. The orthodontic wires or dental implants may be comprised of any metals suitable for use in dental devices, for example stainless steel, titanium, titanium-molybdenum alloy (TMA), beta-titanium, nitinol, alumina, zirconia, nickel-titanium, and alloys and blends of these materials. Beta-titanium, stainless steel and nickel-titanium alloys are currently preferred archwire materials.

Materials useful for the friction-reducing film include hard, relatively inert metals which do not tend to form oxides in the environment of the mouth, biocompatible IF nanoparticles and composites with such nanoparticles. The coated wire of the invention also may include one or more additional intermediate layers between the wire and the outer, function-reducing film. The intermediate layer(s) preferably comprise a metallic material selected from the group consisting of Ni and Ni—Cr.

One method of applying the friction reducing film is by incorporating the IF nanoparticles into a coating by composite electroless deposition. Electroless plating has gained popularity since the beginning of the last century when it was first introduced, due to the production of coatings with excellent corrosion, wear and abrasion resistance. Electroless plating is a chemical process of oxidation and reduction by which a metallic ion is reduced from an aqueous solution containing a reducing agent onto a surface having a catalytic site with no need to transfer a current. Of the variety of metal ions that are in use, nickel and cobalt have proven supremacy in corrosion and wear resistance when deposited as nickel phosphorus (Ni—P), cobalt phosphorus (Co—P), or mixtures of Co—P or Ni—P with other transition metals such as for example Co—Ni—P, Co—Rh—P, Co—W—P or Co—Fe—P. The incorporation of IF-$WS_2$ nanoparticles into Ni—P matrix was carried out by a method similar to that reported by Chen et al [Chen et al, Adv. Eng. Mat. 4(9): 686-690 (2002)].

Another way of coating an article with a friction reducing film is by electrochemical deposition. In this way the article is first exposed to a surface pre-treatment procedure. In the next step, the article is immersed in a metal solution and a current is applied. A similar solution containing IF nanoparticles is then prepared by sonication and the article is immersed in this solution and a current is applied. Alternatively, the article is first immersed in a metal solution, such as Cr or Ti and then in the next step is immersed in another solution of Ni—P or Cr containing the IF nanoparticles.

The metal solution for the electrochemical deposition may be any metal solution. For example, the metal may be Ni, Pt, Co, Cr, Fe, or alloys thereof.

In a preferred embodiment of the invention the article is coated with a polymer (e.g. polyurethane or polypropylene) or epoxy coating. In this embodiment, the polymer is heated until a non-viscous polymer is obtained and then IF-nanoparticles are added. In the next step, the article is painted with the polymer or immersed in the polymeric solution. Then the polymer is treated by curing (radiation) or by cross-linking (e.g. with UV light).

In a further preferred embodiment, a sol-gel glass coating is applied on the article.

Another way of coating an article with a friction reducing film is implemented by burnishing nanoparticles powder with cloth for a few minutes and then burnishing the article with the cloth until a coating of the nanoparticles is applied on the article, which serves as a self-lubricating coating.

Electroless Ni—P Coatings on Stainless Steel (SS) Orthodontic Wires

Figure 2:
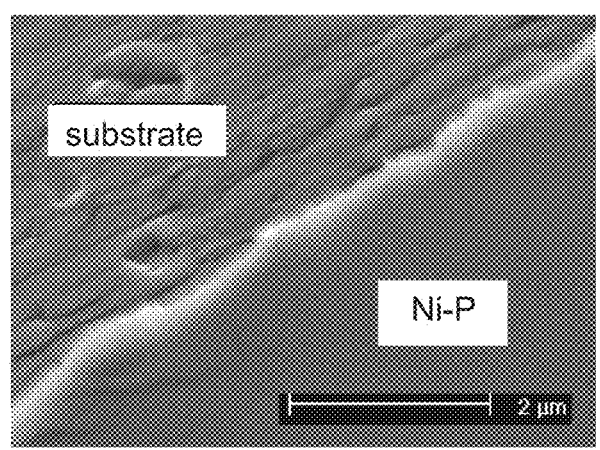
FIG. 2 is a SEM magnification ×12000 of Ni—P coating on SS wire.

FIG. 2 shows a smooth, homogenous film of electroless Ni—P on a stainless steel wire. The scotch bond test caused peeling of the coating, as opposed to a same test carried on a stainless steel plate coated with similar Ni—P film by electroless deposition, indicating poor adhesion to the wire substrate. The SEM images of the two substrates showed different microscopic morphology in spite of having the same SS composition. This difference in the surface morphology is suggested to be the cause to the poor adhesion of Ni—P film exhibited by the wires as opposed to plates.

Electroless Plating Composite of Ni—P with IF-WS$_2$ Particles

Preparation of electroless bath: enabling a mixture of IF-WS$_2$ particles (or other desired IF particles) into the electroless Ni plating solution required the nanoparticles dispersion within the electroless plating bath. This was achieved by agitating a dispersion of the WS$_2$ nanoparticles in the electroless bath (commercially available solution sold under the name Enplate Ni-425, Enthone Inc.) by ultrasonic stirrer and also by the use of suitable surfactants. Among the series of surfactants used, i.e. anionic (SDS-sodium dodecyl sulfate), cationic (CTAB-cetyl trimethyl ammonium bromide) and non-ionic (Triton-x), CTAB seemed to show the best results.

Figure 3A:
FIGS. 3A and 3B show TEM images of single IF-$WS_2$ nanoparticles after ultrasonic dispersion within a Ni—P matrix after 2 minutes of sonification and one hour of plating activity, respectively.
Figure 3B:
Figure 3C:
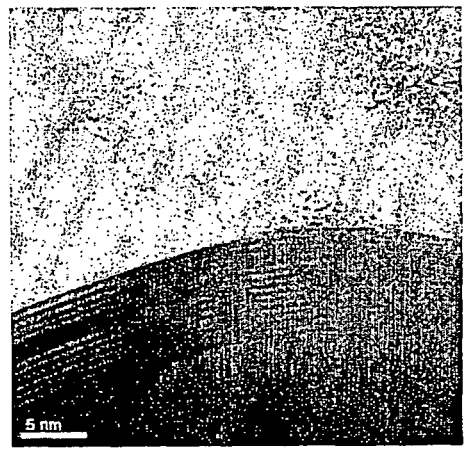
FIGS. 3C and 3D show an enlarged TEM image of the IF where the layers are observed with no apparent damage.
Figure 3D:
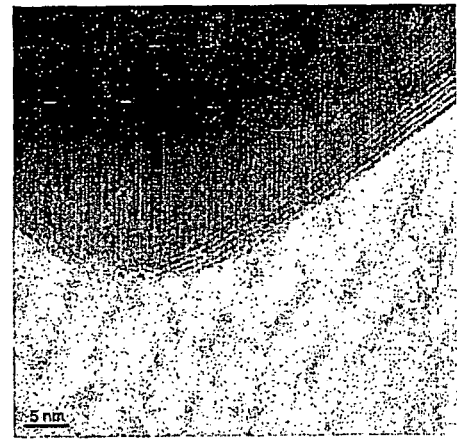

FIGS. 3A and 3B show TEM images of single IF-WS$_2$ nanoparticles after ultrasonic dispersion within a Ni—P matrix after 2 minutes of sonification and one hour of plating activity, respectively. FIGS. 3C and 3D show an enlarged TEM image of the IF where the layers are observed with no apparent damage.

The electroless reaction was carried out first by treating the wire with an HF solution, in order to cause pitting of the substrate and consequently mechanically enhance the adhesiveness of the coating to the wire substrate. In a second step the wire was subjected to electroless coating in a commercially available plating bath containing essentially IF particles, Ni and phosphate, to obtain a wire coated with composite Ni—P-IF-WS$_2$ film that had adequate adhesive strength to the w/e surface (adequate adhesive strength as measured by the scotch-bond test). The thickness of the Ni—P-IF-particles film obtained by the method of the present invention is between about 0.3 microns to about 50 microns, more preferably between about 1 to about 10 microns.

Electroless Plating Composite of Co—P with IF-WS$_2$ Particles

In a similar manner the inventors obtained a composite film of Co—P with IF-WS$_2$ particles, by electroless plating. The plating solution (pH 6.85) consisted of 0.3 M sodium citrate (Na$_3$C$_6$H$_5$O$_7$), 0.1M sodium hypophosphate and 0.1 M ammonium chloride (NH$_4$Cl). The concentration of cobalt (II) chloride (CoCl$_2$) was increased up to 0.1 M. The hydrazine (N$_2$H$_4$) concentration was increased up to 0.3 M. The pH was controlled by increasing the sodium hydroxide (NaOH) concentration up to 1.25 M.

IF-WS$_2$ particles were dispersed in the Co electroless bath by using an anionic surfactant, for example SDS (sodium dodecyl sulfate). A uniform film of Co—P or Co (depending on the existence or absence of sodium hypophosphate in the plating solution) with the IF particles was obtained.

Electrochemical Plating Film of Co with IF-WS$_2$ Particles

A film of Co with IF-WS$_2$ particles was obtained by electrochemical plating. A stainless-steel plate (5×5 mm$^2$) was cleaned first by immersion in HF (20%) solution for 2 min. The plate was subsequently rinsed carefully in water and dried under N$_2$ gas stream. In the next step, the plate was immersed in a solution containing 40 ml CoCl$_2$ 1M (and optionally 40 ml NiCl$_2$ 1M) and 0.2 ml acetic acid was added to the solution to bring the pH to 3.5. A current of 1 mA was applied on the plate which served as cathode with Pt gauge as an anode. The stainless steel plate was rinsed and immersed in a similar solution but now containing 3 wt % of IF-WS$_2$, which was prepared by sonication. A current of 1 mA was applied for 20 second. A black film was obtained. The overall thickness of the film was about 6 micron.

Sol Gel Glass Coating with IF-WS$_2$ Particles

A mother solution of Zirconia is prepared. Glacial acetic acid (3 ml) is slowly added to 10 ml of zirconia tetrapropoxide (Zr(OC$_3$H$_7$)$_4$, TPOZ) and stirred for 30 minutes. Then 20 ml of n-propanol (C$_3$H$_7$OH) is added to the solution, which is further stirred for 15 minutes at room temperature. The solution is hydrolyzed with 4 ml of 50% diluted solution of acetic acid in deionized (DI) water. Following this step, the solution is stirred for another 30 minutes at room temperature, filtered, and stored in a refrigerator for up to 4 days. The solution is transparent and its color pale yellow.

In the next step, alcoholic suspension of the IF-WS$_2$ nanoparticles is prepared by sonication of 10 mg of the nanoparticles and is added dropwise to the stirred mother solution. After that the articles are immersed in the suspension and after withdrawing (dip coating) and drying are annealed in 40° C. for an hour. The final step is annealing of the articles at 300° C. in inert gas atmosphere.

Friction and Wear Testing

The tests were performed using a ball-on-flat device with a sliding velocity of 0.2 mm/s and a load of 50 gr. A bearing ball with a diameter of 2 mm was used as a counter body. Dry and wet friction with paraffin oil lubricant were carried out during 50-200 cycles. Optical magnification of micrographs is ×240.

Figure 4:
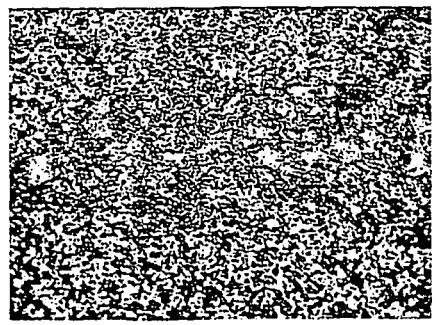
FIG. 4 is an optical micrograph of the surface of a Ni—P-IF-$WS_2$ film, after 100 cycles of dry friction.

The surface of Ni—P-IF-WS$_2$ coating with a wear track after 100 cycles of dry friction is shown in FIG. 4.

In order to simulate the friction behavior of the coatings in the mouth at definite fluid medium, some drops of Mouth Kote (oral moisturizer) have been fed into the interface between the steel ball and the coating. In this experiment the ball used was made of silicone nitride. Corrosion tracks on the surface of the ball were not observed, as can be seen in FIG. 5A. The IF particles are observed on the surface of the silicon nitride ball before cleaning with hexane. No wear track and particles on the surface of the ball were observed after the cleaning, as can be seen in the photograph in FIG. 5B.

In another test the inventors compared the friction coefficient of an uncoated orthodontic wire substrate to that of a wire coated with a composite of Ni—P—WS$_2$. The graph in FIG. 6 shows the results of 30 cycles of this test, from which it is evident that after the first cycle the friction coefficient of the uncoated wire was 0.1 and that of the coated wire was 0.08, while after 30 cycles the uncoated-wire friction coefficient was 0.25 and that of the coated wire was 0.05.

Instron Testing

Figure 7A:
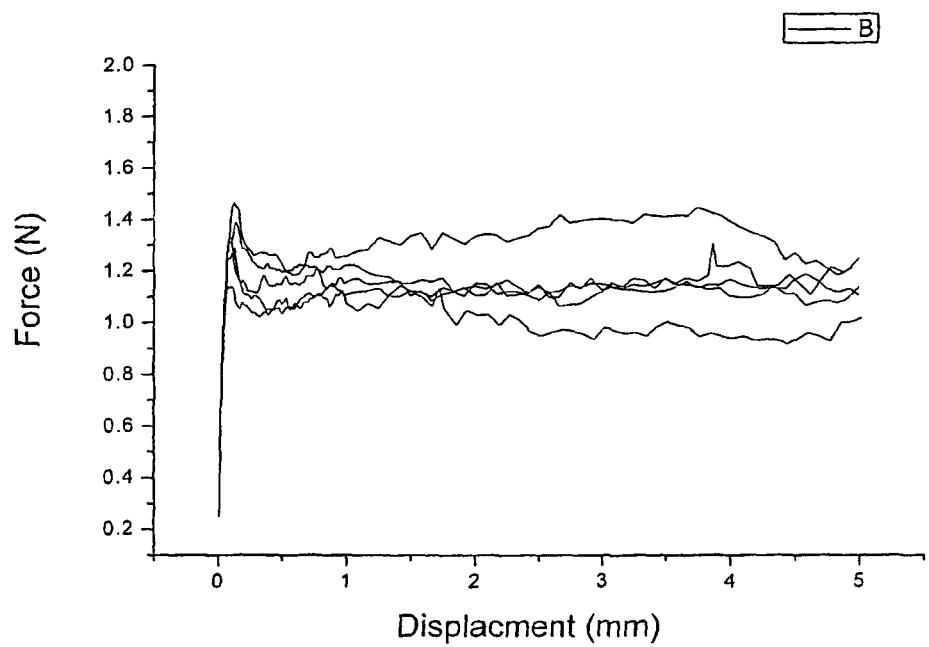
FIG. 7A is a graph of force (N) vs. displacement (mm) in non coated SS wire, taken at 0° angle of contact between the bracket and the wire; average force is 1.32N (STANDARD DEVIATION (SD))=0.12).
Figure 7B:
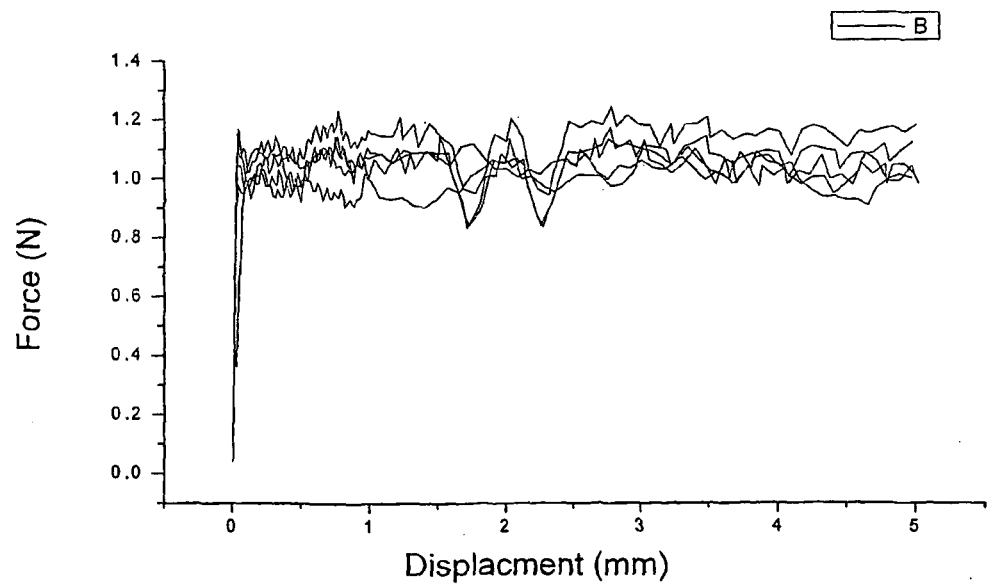
FIG. 7B is a graph of force (N) vs. displacement (mm) in coated wire, taken at 0° angle of contact between the bracket and the wire, tested on the same bracket; average force is 1.10N (SD=0.06).
Figure 8A:
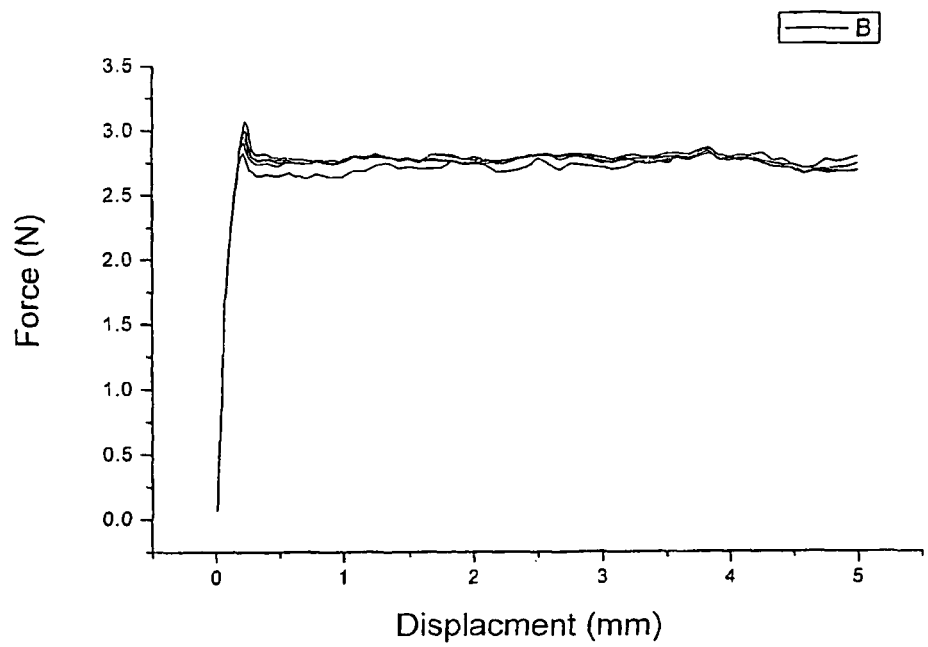
FIG. 8A is a graph of force (N) vs. displacement (mm) in non coated SS wire, taken at 5° angle of contact between the bracket and the wire; average force is 2.95N (SD=0.09).
Figure 8B:
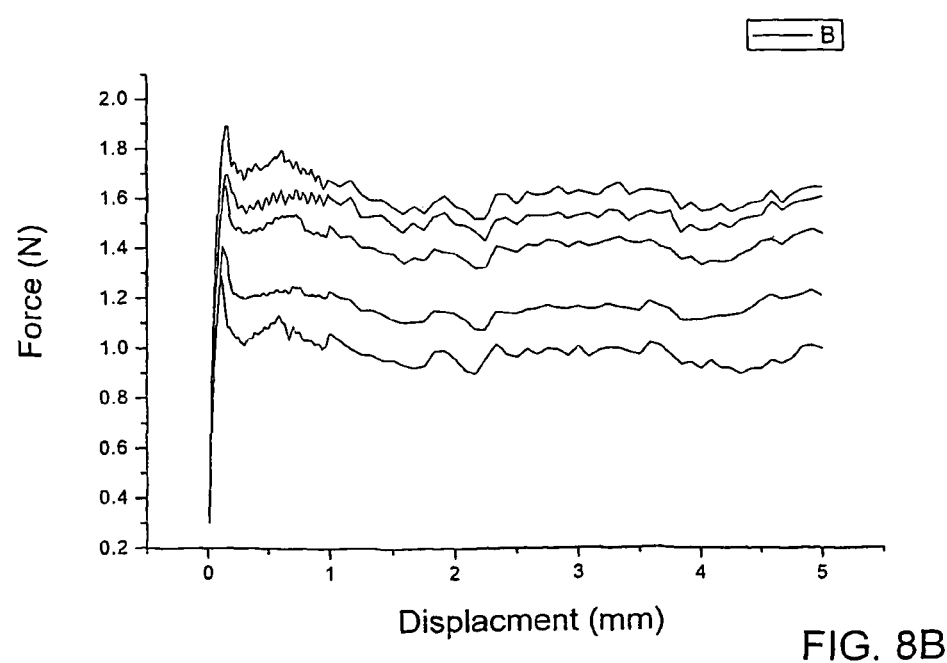
FIG. 8B is a graph of force (N) vs. displacement (mm) in coated wire, taken at 5° angle of contact between the bracket and the wire, tested on the same bracket; average force is 1.58N (SD=0.25).
Figure 9A:
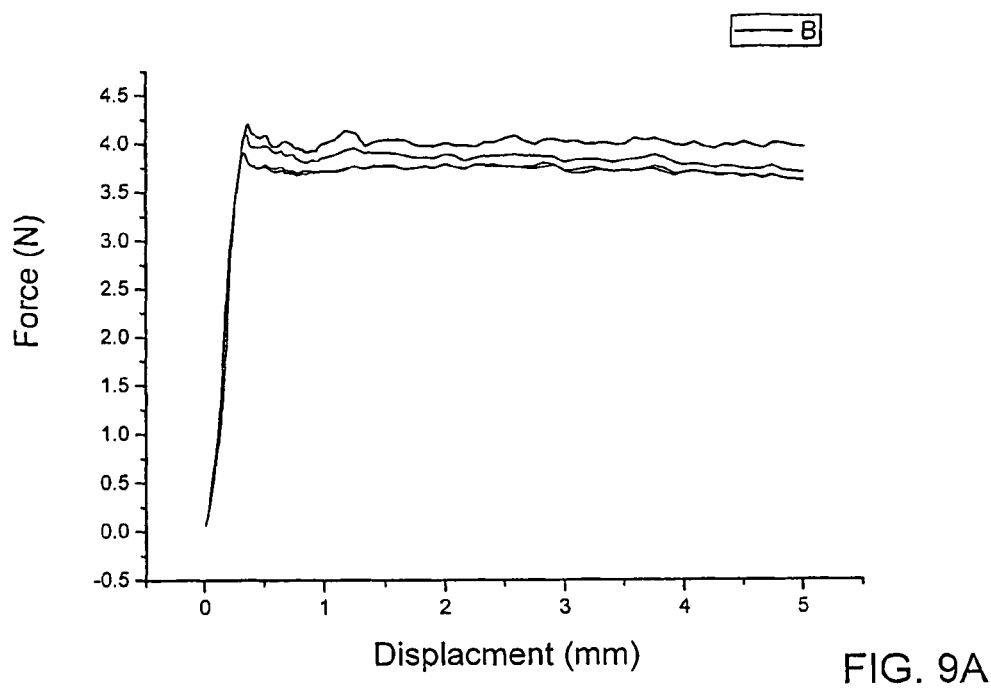
FIG. 9A is a graph of force (N) vs. displacement (mm) in non coated SS wire, tested in dry mode at 10° angle of contact between the bracket and the wire; average force is 4N (SD=0.19).
Figure 9B:
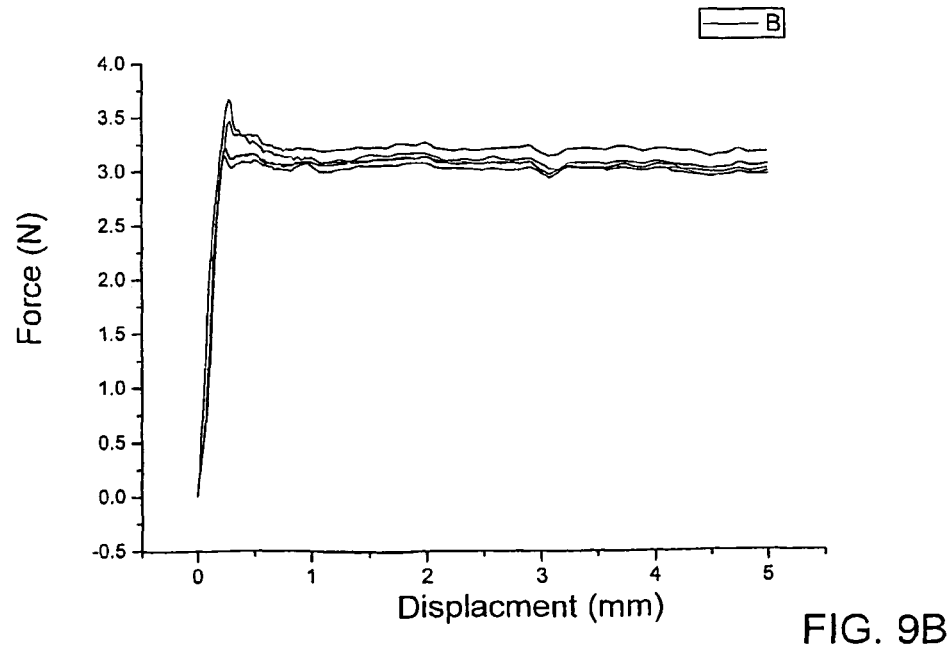
FIG. 9B is a graph of force (N) vs. displacement (mm) in non coated SS wire, tested in wet mode at 10° angle of contact between the bracket and the wire; average force is 3.35N (SD=0.21).
Figure 9C:
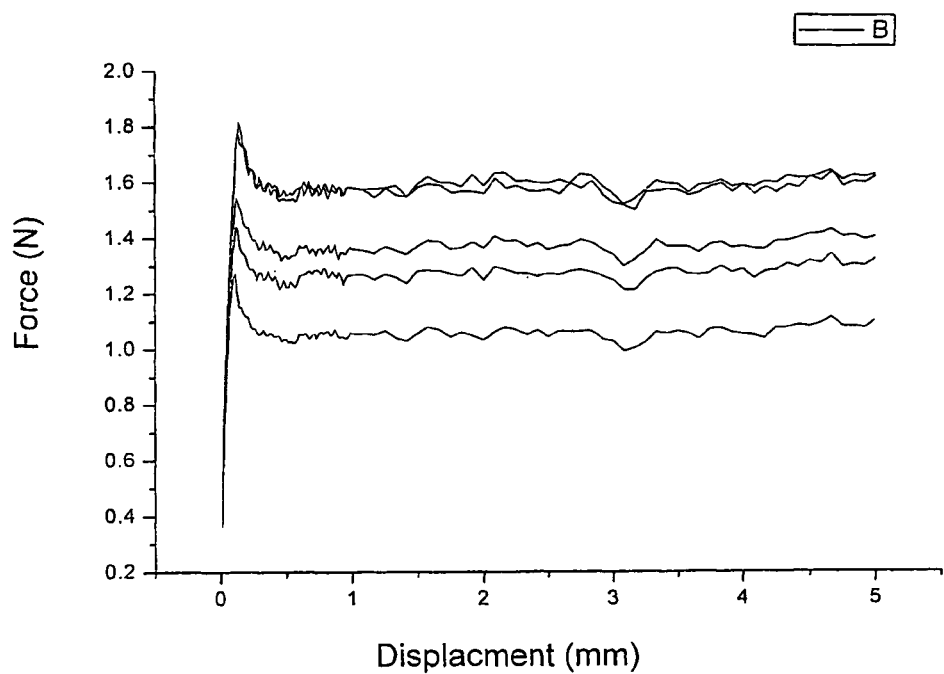
FIG. 9C is a graph of force (N) vs. displacement (mm) in coated wire, tested in wet mode at 10° angle of contact between the bracket and the wire, tested on the same wet bracket; average force is 1.57N (SD=0.23).

The coated wires were compared to uncoated wires at conditions simulating the movement of the tooth and bracket on the wire in the mouth, by using the Instron assembly. The tests were set at 3 different angles of contact between the bracket and the wire. From the results presented in FIG. 6 it was obvious that a run-in period was needed before testing the wires on the Instron. The run-in period of the wire was done by repeated back and forth movements of the wire in a bracket slot before connecting the wire to the Instron. A different bracket was used for the Instron testing. Data is presented in Table I below and comparative graphs in FIGS. 7-9 showing the relation between force and displacement of brackets where the peak indicates the maximum force needed to begin movement of the bracket on the wire (static friction).

TABLE I

Summary of Instron testing. Results or Force are in N ± SD.

| COATING | 0° | 5° Uncoated wire tested first | 5° Coated wire tested first | 10° Uncoated wire tested first | 10° Coated wire tested first |
|---|---|---|---|---|---|
| Non coated wire | 1.32 ± 0.12 | 2.95 ± 0.09 | 2.64 ± 0.16 | 4.00 ± 0.19 Dry<br>3.35 ± 0.21 wet | 2.76 ± 0.26 wet |
| Ni—P + IF coated wire | 1.10 ± 0.06 | 1.58 ± 0.25 | 1.61 ± 0.18 | 1.57 ± 0.23 wet | 1.85 ± 0.21 dry<br>1.85 ± 0.31 wet |

The highest angle of 10° was tested in the dry and wet mode. DI water was used instead of the Mouth Kote lubrication fluid due to the possible damage to the Instron equipment. Angles 5° and 10° were repeated in a reverse order for the purpose of investigating the effect of residual nanoparticles remaining in the bracket slot.

The Instron results show a substantial reduction in the friction resistance to sliding at the different angles that were tested. At an angle of 0° the reduction of friction was 17%. As the angle grew to 5°, the reduction rate grew to 46% and the 10° angle showed a 54% reduction of friction compared to the uncoated wire. Without being bound to theory, the mechanism by which this reduction is achieved may be explained by the theories suggested by Rapoport et al [Rapoport et al., Wear 255, 785-793 (2003)]. At the first stage when there is no angle between the slot and wire, the IF nanoparticles act as spacers and reduce the number of asperities that come in contact resulting in a lower coefficient of function. As the angle grows the load at the edges of the slot increases causing the higher friction levels on the uncoated wire. It is probably at this point on the coated wire that the exfoliation of the nanoparticles occurs, resulting in the dry lubrication of the sliding. The higher load at this point brings the asperities in close contact causing the saliva to be squeezed out of the gap between the wire and slot, relying on the dry lubrication properties of the materials in contact to allow the sliding. When the two materials are stainless steel, as is with the uncoated wire, the friction coefficient is higher. When IF particles are in the interface under high loads, the sliding occurs within these sheets reducing the coefficient of friction.

Conclusions

The tests, carried out on SS plates, resulted in a composite coating of an electroless Ni—P matrix and IF-$WS_2$ nanoparticles dispersed within this matrix. The dynamic coefficient of friction was reduced from 0.6 on the stainless-steel substrate to 0.06 on the coated substrate, Comparing the tribological testing results of the plate substrate to the orthodontic wire shows that the orthodontic wire has an initial low dynamic coefficient of friction (0.1) even though they are composed of the same stainless steel substrate. This perhaps is attributed to the finishing process done by the manufacturer and is evident by the different surface morphologies seen in the SEM images. In spite of the low coefficient of friction, the orthodontic force that is needed in order to move a tooth along an archwire is still much higher than the biological requirement due to the friction force that develops during this movement. The friction coefficient of the wire increases dramatically when the load increases, which was indeed the case when the orthodontic wires were used in realistic conditions (by tilting the bracket). For this reason it is desirable to achieve a reduction in the friction coefficient of the wire. The coating of the wire with the composite Ni—P-IF-$WS_2$ reduced the function coefficient to 0.05 after a run-in period. When the uncoated wire was tested in cycles, the friction coefficient was elevated to 0.25. This could mean that the force needed for orthodontic movement grows with time on the uncoated wire and is reduced with time on the coated one.

Instron tests were carried out in order to simulate the actual type of forces that develop during the orthodontic tooth movement. The Instron simulates the tilt in the wire with respect to the bracket and consequently the entire load is exerted on a small area of the bracket (on the corners), resulting in much higher function. These tests resulted in the reduction of friction on the coated wire, a reduction that is pronounced with the elevation of the angle between the wire and the slot. At an angle of 10°, the force needed to move the bracket along the archwire was 54% lower on the coated wire. Due to the tipping and uprighting type of movement that is encountered during orthodontic treatment, this type of lubrication is most desirable because the main problem of resistance to sliding is found at the angels higher than the critical contact angle.

Tribological tests in the wet mode using a saliva substitute resulted in increased friction coefficients for both coated and uncoated SS plates tested with a tempered steel ball. When the wires were tested on the Instron in the wet mode, using DI water and SS brackets, a reduction in the force (friction) was recorded. This difference is attributed to the corrosion that developed on the tempered steel ball tester and to the fact that a different type of fluid was in use. The reduction observed with the wire and bracket in the Instron was attributed to the lubrication potential of the DI water and the short duration of the test:

The method developed here for coating the orthodontic archwire substrate was aimed at overcoming the poor adhesive strength of the coating to the wire, compared to the SS plates. Use of Ni or Ni—Cr+Ni by e-beam evaporation as an initiator of the electroless process was not sufficient. A conditioning step of etching the substrate by HF was needed for increasing the retention of the coating to the wire. The reason for the difference between the SS plate and the orthodontic wire is probably due to the finishing process and the flexibility of the wire, which can affect the bonding force between the coating and the wire.

The coatings of the invention may be applied to other orthodontic materials as well. A self-ligating bracket, for example, should show even lower friction levels when the coating is in use. Moreover, this coating may be utilized in other biological systems where friction is a problem as in temporomandibular disorders or in hip replacements.

EXPERIMENTAL WORK

Experiments were carried out on orthodontic archwire made of stainless steel (304). To begin the electroless plating process there is a need for preparation of the substrate surface. The first step is degreasing by acetone followed by propanol, water rinse and drying under nitrogen flow. The wire is then treated in a plasma asher (March) for 5 min and a pure nickel film (100 nm) is deposited by e-beam evaporation (Edwards Auto 306).

A commercial (ENPLATE Ni-425, Enthone Inc.) electroless plating Ni—P solution was used for the present experiments for coating the orthodontic wires (sds Ormco, Calif. 0.019×0.025 inch rectangular stainless steel arch wires) and the coating seemed to have poor adhesion as tested by a simple scotch bond test. To overcome this problem a thin film of 80-20% nickel-chromium (Ni—Cr) was deposited by e-beam evaporation instead of a pure Ni film. However the electroless reaction could not be initiated on this film. To overcome this difficulty and initiate the electroless plating, a layer of pure Ni was e-beam evaporated on the Ni—Cr film and plating was achieved. The triple layer coating seemed to have adequate adhesion strength tested by scotch-bond and by bending the wire.

The next step was to add the inorganic fullerene-like nanoparticles of $WS_2$ (IF-$WS_2$) to the electroless plating solution in order to incorporate it into the Ni—P layer. For that purpose, 200 mg of $WS_2$ were added to 100 ml solution and dispersed by a magnetic stirrer. However this process did not result in a stable suspension. The LF-nanoparticles quickly agglomerated and precipitated. To suspend the IF-nanoparticles in the plating bath, a series of surfactants were tested including Triton-x, sodium dodecylsulfate (SDS) and cetyltrimethylammoniumbromide (CTAB). The CTAB cationic surfactant gave the best results but the amount of the agglomerated nanoparticles was still very high. In order to achieve a more stable suspension, an ultrasonic probe (sonifaier 150, Branson-30 watts output) was inserted into the solution for one minute. This resulted in an evenly dispersed solution that was stable for long periods of time. Transmission electron microscopy (model CM120, FED)(TEM) analysis indicated that under these conditions the agglomerates of the IF nanoparticles could be suspended without damaging the nanoparticles.

With this resulting solution, SS wires were coated. First, the wires were treated with 20% HF and were inserted in the electroless bath. In this case a coating of Ni—P-IF-$WS_2$ was accomplished. Having a layer of Ni—Cr and/or Ni underneath the Ni—P-IF-$WS_2$ further improved the continuous properties of the coating. The wires were then annealed at 400° C. in $N_2$ atmosphere for one hour and then tested with a ball on flat tester as described above and compared to the uncoated wires.

Figure 10:
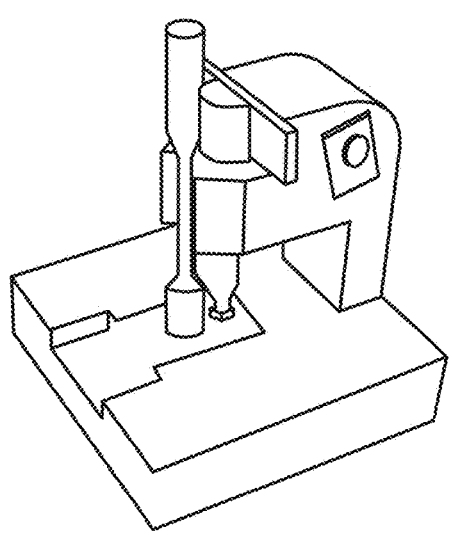
FIG. 10 is a photograph of the bracket-mounting apparatus.
Figure 11:
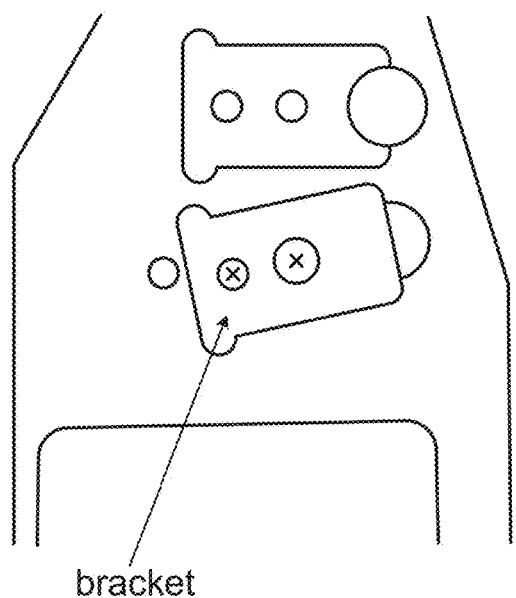
FIG. 11 is a photograph of an angulation device with an aluminum plate screwed in the 10° angle slot.
Figure 12:
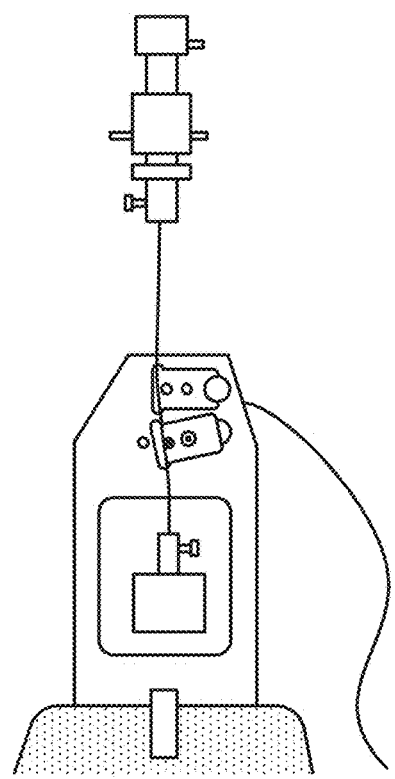
FIG. 12 is a photograph showing an orthodontic wire inserted into the bracket slot and ligated by an elastic module. The wire is connected on the top to the load cell and on the bottom to the 150 g weight.

To simulate the type of movement, which occurs during orthodontic treatment when the sliding of a tooth across an archwire is preformed, a system described by Redlich et al was utilized [Redlich et al., Am. J. Orthod. Dentofacial Orthop. 124, 69-73 (2003)]. Upper right incisor (0.022× 0.028) SS straight wire brackets (GAC, NY) were bonded with cyanoacrylate glue to aluminum plates by a bracket-mounting apparatus (FIG. 10)). This apparatus insures the accurate and similar positioning of the brackets on the plates. These plates were then connected to the base of an INSTRON 4502 testing machine through a device with 3 different notches angulated at 0°, 5° and 10° to the long axis of the device (FIG. 11). Angulations represent the contact angle between the wire and bracket during the movement of the tooth. 12-cm segments of the orthodontic wires (coated & uncoated) were attached, on their upper part, to a 10 Newton load cell and the lower end was connected to a 150 g weight. The wires were then inserted into the slots in the brackets and ligated with an elastomeric module (Sani-Ties Silvar, GAC) to all 4 wings of the brackets (FIG. 12).

In this setup the Instron was set to move the bracket down along the wire at a constant speed of 10 nm/min to a distance of 5 mm. The test begins with a steady increase in the force and reaches a maximum when movement begins on the wire. This maximum represents the static friction and is the force that is of interest in this case.

Uncoated and coated wires were tested at the 3 different angles. The first tests on the coated wires resulted in high friction levels that were overcome by a run-in period of repeated back and forth movements of the wire in the bracket. At the highest angle (10°) the tests were further conducted in a wet mode with DI water dripping on the bracket and wire during the test simulating the saliva in the interface when the movement occurs in the mouth. The tests were repeated 5 times for each group and all the data was recorded onto the operating system of the INSTRON and then analyzed and plotted.

Biocompatibility Tests and Results

Toxicology tests of the IF-$WS_2$ reported the material as being non-toxic in an oral administration in rats. The presence of Ni in orthodontic appliances is known and they are approved for use (except in people with an allergic sensitivity to Ni).

Experimental Design Conditions:
Replace Table—not Clear
1. Constitution of Test Groups and Dose Levels:

| | | | TREATMENT | | | |
|---|---|---|---|---|---|---|
| Group No. & General[d] | Group Size[d] | Individual Animal No.'s | Test Compound | Route | Dose (mg/kg) | Volume Dosage (ml/kg) |
| 1F | n = 6 | 1, 2, 3, 4, 5, 6 | Inorganic fullerene-like $WS_2$ nanospheres (IF-$WS_2$) | PO | 300 | 5 ml/kg |
| 2F | n = 6 | 7, 8, 9, 10, 11, 12 | | | 2000 | |

2. Principles of the Test:

Due to the lack of information regarding potential toxicity, and in accordance with the Guideline recommendation, the sequential method applied in this study represents a stepwise procedure, using a minimum amount of animals. Dosing was sequential and the time interval between the test groups dosing was determined by the lack of adverse effects following dosing.

3. Administration:

3.1 Route of Administration:

All animals were subjected to a single oral gavage (PO) administration.

3.2 Dose Levels:

The Test Item as supplied by the Sponsor was administered at two dose levels of 300 and 2000 mg/kg.

3.3 Volume Dosage:

In all instances the volume dosage was 5 ml/kg.

4. Justification for Route of Administration and Dose Levels:

The oral route was chosen as the route of administration since in order to assess the toxic characteristics of substances the determination of acute oral toxicity is usually an initial step. The initial dose level selected was based on the Sponsor's specific request and according to the respective guideline.

5. Observations and Examinations:

5.1 Clinical Signs:

Animals were observed continuously during the first 7-8 hours following dosing and then periodically during the first 24 hours. Clinical signs were recorded. Animals were observed for a total during of 14 days. Observations included that of the skin, fur, eyes, mucous membranes, occurrence of secretions and excretions (e.g. diarrhea) and autonomic activity (e.g. lacrimation, salivation, piloerection, pupil size, unusual respiratory pattern). Additional items that were observed were the gait, posture and response to handling, as well monitoring for any presence of bizarre behavior, tremors, convulsions, sleep and coma.

5.2 Body Weight:

Determination of individual body weights of animals was made shortly before Test Item administration, 2 and 7 days following dosing and at the end of the study prior to the scheduled necropsy.

6. Necropsy Procedures and Macroscopic Examination:

All test animals were subjected to full detailed macroscopic necropsy. All gross pathological changes were recorded for each animal.

Data Evaluation:

Evaluation included monitoring the relationship, if any, between the animals' exposure to the Test Item and the incidence and severity of all abnormalities including: effects on mortality, behavioral and clinical abnormalities, body weight changes, gross lesions, and any other toxic effects.

Animal Care and Use Statement:

Results:

1. Mortality (Table 1):

No mortality occurred in any of the animals throughout the entire 14-day observation period.

2. Clinical Signs (Table 2):

No noticeable clinical signs in reaction to dosing were evident in any of the animals administered with Inorganic fullerene-like $WS_2$ nanospheres (IF=$WS_2$) at the immediate post-dosing period or during the entire 14-day observation period.

3. Body Weight (Table 3-5):

Body weight gain of all animals was found to be within range of normally expected values.

4. Macroscopic Examination: (Table 6):

No pathological changes were observed in any of the animals during necropsy procedure.

CONCLUSION

In consideration of the lack of mortality at dose levels of 300 and 2000 mg/kg PO (oral administration), the Test Item Inorganic fullerene-like $WS_2$ nanospheres (IF-$WS_2$) is allocated to "Category 5" or "Unclassified" in accordance with the classification by GHS (Globally Harmonized System) (e)

TABLE 1

Mortality Incidence Observed throughout the Entire 14-day Observation Period, in Female Sprague-Dawley ™ Rats, Following a Single Oral Administration of Inorganic fullerene-like $WS_2$ nanospheres (IF-$WS_2$) (Batch No.: HP6):

| Group No. & Gender | Group Size | Test Material | MORTALITY (Number affected/ Total number of animals) |
|---|---|---|---|
| 1F | n = 6 | Inorganic fullerene-like $WS_2$ nanospheres (IF-$WS_2$) (300 mg/kg) | 0/6 |
| 2F | n = 6 | Inorganic fullerene-like $WS_2$ nanospheres (IF-$WS_2$) (2000 mg/kg) | 0/6 |

TABLE 2

Individual Clinical Signs Observed throughout the Entire 14-day Observation Period, in Female Sprague-Dawley ™ Rats, Following a Single Oral Administration of Inorganic fullerene-like $WS_2$ nanospheres (IF-$WS_2$):

| Group No. & Gender | Individual Animal No. | Test Material | OBSERVATION (Number affected/ Total number of animals) | |
|---|---|---|---|---|
| | | | Day of Dosing (Day 0) | Day 1-13 |
| 1F | 1 | Inorganic fullerene- like $WS_2$ nanospheres (IF-$WS_2$) (300 mg/kg) | NAD | NAD |
| | 2 | | NAD | NAD |
| | 3 | | NAD | NAD |
| | 4 | | NAD | NAD |
| | 5 | | NAD | NAD |
| | 6 | | NAD | NAD |
| 2F | 7 | Inorganic fullerene- like $WS_2$ nanospheres (IF-$WS_2$) (2000 mg/kg) | NAD | NAD |
| | 8 | | NAD | NAD |
| | 9 | | NAD | NAD |
| | 10 | | NAD | NAD |
| | 11 | | NAD | NAD |
| | 12 | | NAD | NAD |

NAD = No Abnormality Detected

TABLE 3

Individual and Mean (±SD) Group Values of body Weights in Female Sprague-Dawley ™ Rats, Following a Single Oral Administration of Inorganic fullerene-like $WS_2$ nanospheres (IF-$WS_2$):

| Group No. & Gender | Test Material | Individual Animal No. | Body Weight (g) Day 0 | Day 2 | Day 7 | Day 14 |
|---|---|---|---|---|---|---|
| 1F | Inorganic-fullerene-like $WS_2$ nanospheres (IF-$WS_2$) (300 mg/kg) | 1 | 177 | 194 | 209 | 228 |
| | | 2 | 183 | 203 | 225 | 233 |
| | | 3 | 173 | 192 | 205 | 222 |
| | | 4 | 185 | 202 | 213 | 231 |
| | | 5 | 182 | 196 | 207 | 225 |
| | | 6 | 186 | 209 | 213 | 228 |
| | | Mean | 181 | 199 | 212 | 228 |
| | | | (n = 6) | (n = 6) | (n = 6) | (n = 6) |
| | | ±SD | 5.0 | 6.4 | 7.1 | 4.0 |
| 2F | Inorganic-fullerene-like $WS_2$ nanospheres (IF-$WS_2$) (2000 mg/kg) | 7 | 190 | 207 | 212 | 223 |
| | | 8 | 194 | 206 | 211 | 223 |
| | | 9 | 209 | 217 | 228 | 238 |
| | | 10 | 195 | 208 | 222 | 235 |
| | | 11 | 195 | 213 | 222 | 233 |
| | | 12 | 199 | 214 | 228 | 231 |
| | | Mean | 197 | 211 | 221 | 231 |
| | | | (n = 6) | (n = 6) | (n = 6) | (n = 6) |
| | | ±SD | 6.5 | 4.4 | 7.5 | 5.3 |

TABLE 4

Individual and Mean (±SD) Group Values of Body Weight Gain (g) in Female Sprague-Dawley ™ Rats, Following a Single Oral Administration of Inorganic fullerene-like $WS_2$ nanospheres (IF-$WS_2$) (Batch No.: HP6):

| Group No. & Gender | Test Material | Individual Animal No. | Body Weight (g) Day 0-2 | Day 2-7 | Day 7-14 | Day 0-14 |
|---|---|---|---|---|---|---|
| 1F | Inorganic-fullerene-like $WS_2$ nanospheres (IF-$WS_2$) (300 mg/kg) | 1 | 17 | 15 | 19 | 51 |
| | | 2 | 20 | 22 | 8 | 50 |
| | | 3 | 19 | 13 | 17 | 49 |
| | | 4 | 17 | 11 | 18 | 46 |
| | | 5 | 14 | 11 | 18 | 43 |
| | | 6 | 23 | 4 | 15 | 42 |
| | | Mean | 18 | 13 | 16 | 47 |
| | | | (n = 6) | (n = 6) | (n = 6) | (n = 6) |
| | | ±SD | 3.1 | 5.9 | 4.1 | 3.8 |
| | Inorganic-fullerene-like $WS_2$ nanospheres (IF-$WS_2$) (2000 mg/kg) | 7 | 17 | 5 | 11 | 33 |
| | | 8 | 12 | 5 | 12 | 29 |
| | | 9 | 8 | 11 | 10 | 29 |
| | | 10 | 13 | 14 | 13 | 40 |
| | | 11 | 18 | 9 | 11 | 38 |
| | | 12 | 13 | 14 | 3 | 32 |
| | | Mean | 14 | 10 | 10 | 34 |
| | | | (n = 6) | (n = 6) | (n = 6) | (n = 6) |
| | | ±SD | 3.7 | 4.1 | 3.6 | 4.6 |

TABLE 5

Individual and Mean (±SD) Group Values of Percentage (%) Body Weight Gain in Female Sprague-Dawley ™ Rats, Following a Single Oral Administration of Inorganic fullerene-like $WS_2$ nanospheres (IF-$WS_2$) (Batch No.: HP6):

| Group No. & Gender | Test Material | Individual Animal No. | Body Weight (g) Day 0-2 | Day 2-7 | Day 7-14 | Day 0-14 |
|---|---|---|---|---|---|---|
| 1F | Inorganic-fullerene-like $WS_2$ nanospheres (IF-$WS_2$) (300 mg/kg) | 1 | 9.6 | 7.7 | 9.1 | 28.8 |
| | | 2 | 10.9 | 10.8 | 3.6 | 27.3 |
| | | 3 | 11.0 | 6.8 | 8.3 | 28.3 |
| | | 4 | 9.2 | 5.4 | 8.5 | 24.9 |
| | | 5 | 7.7 | 5.6 | 8.7 | 23.6 |
| | | 6 | 12.4 | 1.9 | 7.0 | 22.6 |

TABLE 5-continued

Individual and Mean (±SD) Group Values of Percentage (%) Body Weight Gain in Female Sprague-Dawley ™ Rats, Following a Single Oral Administration of Inorganic fullerene-like $WS_2$ nanospheres (IF-$WS_2$) (Batch No.: HP6):

| Group No. & Gender | Test Material | Individual Animal No. | Body Weight (g) | | | |
|---|---|---|---|---|---|---|
| | | | Day 0-2 | Day 2-7 | Day 7-14 | Day 0-14 |
| | | Mean | 10 | 6 | 8 | 26 |
| | | | (n = 6) | (n = 6) | (n = 6) | (n = 6) |
| | | ±SD | 1.6 | 2.9 | 2.1 | 2.6 |
| 2F | Inorganic-fullerene-like $WS_2$ nanospheres (IF-$WS_2$) (2000 mg/kg) | 7 | 8.9 | 2.4 | 5.2 | 17.4 |
| | | 8 | 6.2 | 2.4 | 5.7 | 14.9 |
| | | 9 | 3.8 | 5.1 | 4.4 | 13.9 |
| | | 10 | 6.7 | 6.7 | 5.9 | 20.5 |
| | | 11 | 9.2 | 4.2 | 5.0 | 19.5 |
| | | 12 | 7.5 | 6.5 | 1.3 | 16.1 |
| | | Mean | 7 | 5 | 5 | 17 |
| | | | (n = 6) | (n = 6) | (n = 6) | (n = 6) |
| | | ±SD | 2.0 | 1.9 | 1.7 | 2.6 |

TABLE 6

Individual Gross Necropsy Findings in Female Sprague-Dawley ™ Rats, Following a Single Oral Administration of Inorganic fullerene-like $WS_2$ nanospheres (IF-$WS_2$) (Batch No.: HP6):

| Group No. | TREATMENT | Animal No. | OBSERVATION |
|---|---|---|---|
| | Inorganic-fullerene-like $WS_2$ nanospheres (IF-$WS_2$) (300 mg/kg) | 1 | NAD |
| | | 2 | NAD |
| | | 3 | NAD |
| | | 4 | NAD |
| | | 5 | NAD |
| | | 6 | NAD |
| | Inorganic-fullerene-like $WS_2$ nanospheres (IF-$WS_2$) (2000 mg/kg) | 7 | NAD |
| | | 8 | NAD |
| | | 9 | NAD |
| | | 10 | NAD |
| | | 11 | NAD |
| | | 12 | NAD |

SUMMARY

1. The potential acute toxicity of the Test Item Inorganic fullerene-like $WS_2$ nanospheres (IF-$WS_2$) (Batch No. HP6) was assessed on the basis of the testing procedure recommended by OECD Guideline for the Testing of Chemicals, Section 4, No. 423, "Acute Oral Toxicity—Acute Toxic Class Method", adopted December $17^{th}$, 2001.
2. Inorganic fullerene-like $WS_2$ nanospheres (IF-$WS_2$) (Batch No. HP6) was administered successively to two groups of n=6 female Sprague-Dawley™ (SD™) rats per each dose levels of 300 and 2000 mg/kg.
3. Animals were observed for a total duration of 14 days following dosing.
4. Body weight gain of all animals was found to be within range of normally expected values[b].
5. No mortality occurred in any of the animals throughout the entire 14-day study period.
6. No adverse signs in reaction to treatment were evident in any of the animals during the immediate post-dosing times or throughout the entire 14-day observation period.
7. No gross pathological findings were noted in any of the animals by necropsy inspection.
8. In consideration of the lack of mortality at dose levels of 300 and 2000 mg/kg PO (oral administration), the Test Item Inorganic fullerene-like $WS_2$ nanospheres (IF-$WS_2$) (Batch No. HP6) is allocated to "Category 5" or "Unclassified" in accordance with the classification by GHS (Globally Harmonized System)[c].

The invention claimed is:

1. An article, comprising:
an exposed surface of the article, at least a portion of the exposed surface of the article being coated by a composite comprising inorganic fullerene-like (IF) nanoparticles in a matrix, the article being suitable for use in medicine or dentistry.

2. The article according to claim 1, wherein the article is in an elongated shape.

3. The article according to claim 2, wherein the article is in a form of wire or tube.

4. The article according to claim 1, wherein the article is circular or rectangular in cross-section.

5. The article according to claim 1, wherein the composite configured to reduce friction between a coated surface of the article and an adjacent object, surface or tissue, as compared to an uncoated surface of the article.

6. The article according to claim 1, wherein the composite is selected from the group consisting of a Ni—P-IF-nanoparticle composite, a Co—P—IF-nanoparticle composite, a Co—B-IF-nanoparticle composite, a Ni—B-IF-nanoparticle composite, a metal film-IF composite, a polyurethane-IF composite, a polypropylene-IF composite, an epoxy-IF composite and a sol-gel glass-IF composite.

7. The article according to claim 1, wherein the IF nanoparticles comprise metal chalcogenide or metal dichalcogenide.

8. The article according to claim 1, wherein the IF nanoparticles comprise one or more compound selected from the group consisting of $TiS_2$, $TiSe_2$, $TiTe_2$, $WS_2$, $WSe_2$, $WTe_2$, $MoS_2$, $MoSe_2$, $MoTe_2$, $SnS_2$, $SnSe_2$, $SnTe_7$, $RuS_2$, $RuSe_2$, $RuTe_2$, GaS, GaSe, GaTe, InS, InSe, $HfS_2$, $ZrS_2$, $VS_2$, $ReS_2$ and $NbS_2$.

9. The article according to claim 6, wherein the composite comprises (i) Ni—P, Co—P, Co—B or Ni—B matrix, and (ii) IF-$WS_2$ or IF-$MoS_2$ nanoparticles.

10. The article according to claim 6, wherein the IF-nanoparticles are IF-$WS_2$ or IF-$MoS_2$ nanoparticles.

11. The article according to claim 1, wherein the composite is biocompatible.

12. The article according to claim 1, wherein the composite has a thickness of between 0.3 micron and 50 microns.

13. The article according to claim 12, wherein the composite has a thickness of between 1 micron and 10 microns.

14. The article according to claim 1, wherein the article is selected from the group consisting of a dental implant, a needle, a catheter, an orthodontic wire, an orthodontic bracket, a band, a bonded or banded orthodontic attachment, a palatal expander, a mobile functioning native or artificial human joint, a hip replacement, a tissue-penetrating device, an oral or nasal feeding tube and a tube used for laparoscopic surgery.

15. The article according to claim 14, wherein the article is an orthodontic archwire.

16. The article according to claim 14, wherein the article is a needle or catheter.

17. The article according to claim 14, wherein the article is a screw-type dental implant.

18. The article according to claim 1, wherein the article further comprises a material selected from the group consisting of metal, rubber, glass and plastic.

19. Method for coating an article of claim 1 for use in medicine or dentistry with a friction reducing film comprising: (i) dispersing IF nanoparticles within a matrix to obtain IF nanoparticles homogeneously dispersed in said matrix; (ii) contacting the article with said matrix and depositing said nanoparticles on one or more surfaces of said article through electroless or electrochemical deposition, thereby obtaining said article.

20. Method according to claim 19, comprising, prior to said contacting, exposing said article to a surface pre-treatment procedure.

21. Method according to claim 20, wherein the surface pre-treatment procedure is carried out with an etching acidic solution.

22. Method according to claim 21, wherein said acidic solution is HF.

23. Method according to claim 19, comprising one or more additional deposition steps prior to said contacting to form intermediate layers between the article and the outer, function-reducing film.

24. Method according to claim 19, further comprising annealing the coated article at high temperature.

25. Method according to claim 19, wherein said article is made of metal and said coating comprises a friction reducing film comprising composite of Ni—P, Co—B, Ni—B or Co—P and IF nanoparticles.

26. Method according to claim 19, wherein said friction reducing film has a thickness of between 0.3 micron and 50 microns.

27. An article, comprising:
at least one material selected from the group consisting of metal, rubber, glass and plastic, the at least one material having an exposed surface, at least a portion of the exposed surface of the article being coated by a composite comprising inorganic fullerene-like (IF) nanoparticles in a matrix.

28. An article selected from the group consisting of a dental implant, a needle, a catheter, an orthodontic wire, an orthodontic bracket, a hand, a bonded or handed orthodontic attachment, a palatal expander, a mobile functioning native or artificial human joint, a hip replacement, a tissue-penetrating device, an oral or nasal feeding tube and a tube used for laparoscopic surgery, the article comprising:
an exposed surface of the article, at least a portion of the exposed surface being coated by a composite comprising inorganic fullerene-like (IF).

* * * * *